(12) United States Patent
Yang et al.

(10) Patent No.: US 8,889,928 B2
(45) Date of Patent: Nov. 18, 2014

(54) METHOD TO IMPROVE 1,1,3-TRICHLOROPROPENE AND/OR 3,3,3-TRICHLOROPROPENE SELECTIVITY DURING THE DEHYDROCHLORINATION OF 1,1,1,3-TETRACHLOROPROPANE

(71) Applicant: Honeywell International Inc., Morristown, NJ (US)

(72) Inventors: Terris Yang, East Amherst, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/796,558

(22) Filed: Mar. 12, 2013

(65) Prior Publication Data
US 2014/0275659 A1 Sep. 18, 2014

(51) Int. Cl.
C07C 17/25 (2006.01)
C07C 21/04 (2006.01)
C07C 19/01 (2006.01)

(52) U.S. Cl.
CPC ............... C07C 17/25 (2013.01); *C07C 21/04* (2013.01); *C07C 19/01* (2013.01)
USPC .......................................... 570/227; 570/226

(58) Field of Classification Search
CPC ........................................................ C07C 17/25
USPC ........................................ 570/156, 155, 135
See application file for complete search history.

(56) References Cited

U.S. PATENT DOCUMENTS

| | | |
|---|---|---|
| 4,535,194 A | 8/1985 | Woodard |
| 4,650,914 A | 3/1987 | Woodard |
| 6,534,688 B2 | 3/2003 | Klausmeyer |
| 7,795,480 B2 * | 9/2010 | Merkel et al. ................. 570/155 |
| 2012/0142980 A1 | 6/2012 | Nappa et al. |
| 2012/0142981 A1 | 6/2012 | Souda et al. |

FOREIGN PATENT DOCUMENTS

| | | | |
|---|---|---|---|
| CN | 101906080 A | * | 12/2010 |
| JP | 2010229047 A | | 10/2010 |
| JP | 2012097017 A | | 5/2012 |
| WO | 2013022676 A1 | | 2/2013 |

OTHER PUBLICATIONS

CN101906080A (English translation pp. 1-19).*
PCT ISR & Written Opinion issued in PCT/US2014/020126 dated Jun. 20, 2014.

* cited by examiner

*Primary Examiner* — Jafar Parsa
*Assistant Examiner* — Medhanit Bahta
(74) *Attorney, Agent, or Firm* — Bruce O. Bradford

(57) ABSTRACT

This invention relates to a method to improve 1,1,3-trichloropropene (HCC-1240za) and/or 3,3,3-trichloropropene (HCC-1240zf) selectivity in the dehydrochlorination of 1,1,1,3-tetrachloropropane (HCC-250fb). In normal practice, $FeCl_3$ is used as the catalyst for the dehydrochlorination of HCC-250fb to produce 1,1,3-trichloropropene and/or 3,3,3-trichloropropene. The present invention demonstrates that when using $FeCl_3$ as the catalyst for 1,1,1,3-tetrachloropropane dehydrochlorination, the reaction product contains significant amounts of high boiling compounds, such as pentachlorocyclohexene and/or hexachlorocyclohexane species. The addition of one or more UV-stabilizer and/or anti-oxidant compounds, or mixtures thereof, into the dehydrochlorination reaction system, inhibits the formation of these high boiling compounds and improves selectivity to the desired product.

20 Claims, No Drawings

METHOD TO IMPROVE 1,1,3-TRICHLOROPROPENE AND/OR 3,3,3-TRICHLOROPROPENE SELECTIVITY DURING THE DEHYDROCHLORINATION OF 1,1,1,3-TETRACHLOROPROPANE

BACKGROUND OF THE INVENTION

The compound 1,1,3-trichloropropene is useful as a chemical intermediate in the formation of other commercially important compounds. See, for example, U.S. Patent Pub. No. 2012-0142980, the disclosure of which is hereby incorporated herein by reference.

SUMMARY OF THE INVENTION

This invention relates to a method to improve the selectivity to the isomeric compounds, 1,1,3-trichloropropene and/or 3,3,3-trichloropropene, by the catalytic dehydrochlorination of 1,1,1,3-tetrachloropropane (HCC-250fb). In normal practice, $FeCl_3$ is used as the catalyst for the dehydrochlorination of HCC-250fb to produce these compounds. See, for example, US Patent Pub. No. 2012-0035402, the disclosure of which is hereby incorporated herein by reference.

It has been discovered that when using only $FeCl_3$ as the catalyst for the dehydrochlorination of 250fb, the reaction products often contain significant amounts of unwanted high boiling compounds ("HBCs") such as pentachlorocyclohexene and/or hexachlorocyclohexane species, in addition to the desired products, namely 1,1,3-trichloropropene and/or 3,3,3-trichloropropene. While not wishing to be bound by any theory, it is believed that the formation of these HBCs is due to the dimerization of the desired compounds. The presence of these HBCs reduces the selectivity to the desired products.

Surprisingly, it has been discovered that the addition of one or more UV-stabilizer and/or anti-oxidant compounds to the dehydrochlorination process of a chlorinated alkane can inhibit the formation of unwanted HBCs and improve the selectivity to the target product significantly Inhibition of HBCs is beneficial to the reduction of process waste and simplifies the separation of the reaction products, and therefore reduces the overall production costs.

The dehydrochlorination reaction is preferably carried out under conditions to attain a starting material HCC-250fb conversion of at least about 20% or higher, preferably at least about 40% or higher, and even more preferably at least about 60% or higher, and a desired product selectivity of at least about 50% or higher, preferably at least about 70% or higher, and more preferably at least about 95% or higher. Selectivity is calculated by the number of moles of product formed divided by the number of moles of reactant consumed.

DETAILED DESCRIPTION OF THE INVENTION

As described above, this invention relates to a method to improve 1,1,3-trichloropropene (HCC-1240za) and/or 3,3,3-trichloropropene (HCC-1240zf) selectivity in the dehydrochlorination of 1,1,1,3-tetrachloropropane (HCC-250fb). In normal practice, $FeCl_3$ is used as the catalyst for the dehydrochlorination of HCC-250fb to produce 1,1,3-trichloropropene and/or 3,3,3-trichloropropene.

The present invention is based on the discovery that when one or more compounds known as UV-stabilizers and/or anti-oxidants is added into a reaction system for the dehydrochlorination of 1,1,1,3-tetrachloropropane using $FeCl_3$ as the dehydrochlorination catalyst, the selectivity to 1,1,3-trichloropropene was significantly improved. In some embodiments, the selectivity to HBCs was reduced to zero when a sufficient amount of a UV-stabilizer and/or anti-oxidant compound was added into the reaction system. These results demonstrate that UV-stabilizer and/or anti-oxidant compounds are suitable for use as inhibitors to control the formation of HBCs during the catalytic dehydrochlorination of 1,1,1,3-tetrachloropropane, when using $FeCl_3$ as the catalyst.

Applicants believe that all of the known UV-stabilizer and/or anti-oxidant compounds, such as benzophenones, polyphenols, amines, hydroquinones, methoxy-hydroquinones, triethylamines, di-isopropyl amines, butylated hydroxy anisoles (BHA) and thymols and the like, as well as mixtures thereof, can be used to inhibit the formation of HBCs in the catalytic dehydrochlorination process of a chlorinated alkane compound. In the examples which follow, the compounds 2,6-di-tert-butyl-p-cresol (butylated hydroxytoluene or BHT), 2,4-di-tert-butylphenol and 2,6-di-tert-butylphenol were used. For example, the dehydrochlorination of 1,1,1,2,3-pentachloropropane to produce 1,1,2,3-tetrachloropropene, can be improved to reduce the formation of HBCs, by the addition of one or more of these UV-stabilizer and/or anti-oxidant compounds.

Applicants also believe that, one or more metal halides or mixtures thereof, such as $FeCl_3$ and/or $FeCl_2$, can be used as the catalyst for the catalytic dehydrochlorination process of a chlorinated alkane compound, with one or more known UV-stabilizer and/or anti-oxidant compounds, as well as mixtures thereof, added into the system to inhibit the formation of HBCs.

Well known UV-stabilizer and antioxidant compounds include, but not limited to, 2,2-biphenyldiols, 4,4-biphenyldiols, isopropyl-meta cresol, tocophenol, hydroquinone, tert-butyl hydroquinone, 2,4-di-tert-butylphenol, 2,6-di-tert-butylphenol, 2,6-di-tert-butyl-p-cresol, 2,6-di-tert-butyl-4-methylphenol, 2,6-di-tert-butyl-4-ethylphenol, 2,4-dimethyl-6-tert-butylphenol, 2,6-di-tert-a-dimethlyamino-p-cresol, 4,4'-thiobis(2-methyl-6-tert-butylphenol), 4,4'-thiobis(3-methyl-6-tert-butylphenol), 2,2'-thiobis(4-methyl-6-tert-butylphenol), 4,4'-methylenebis(2,6-di-tert-butylphenol), 4,4'-bis(2,6-di-tert-butylphenol), 2,2'-methylenebis(6-tert-butyl-4-ethylphenol), 2,2'-methylenebis(6-tert-butyl-4-methylphenol), 4,4-butylidenebis(3-methyl-6-tert-butylphenol), 4,4-isopropyl-idenebis(2,6-di-tert-butylphenol), 2,2'-methylenebis(4-methyl-6-nonylphenol), 2,2'-isobutylidenebis(4,6-dimethylphenol), 2,2'-methylenebis(4-methyl-6-cyclohexyl-phenol), 2,2'-ethylidene-bis(4,6-di-tert-butylphenol), 2,6-di-tert-butyl-4-(N,N'-dimethyl-aminomethyl)-phenol, 4-allyloxy-2-hydroxybenzophenone, 2-(2H-benzotriazol-2-yl)-4,6-bis(1-methyl-1-phenylethyl)phenol, 2-(2H-benzotriazol-2-yl)-4,6-di-tert-pentylphenol, 2-(2H-benzotriazol-2-yl)-6-dodecyl-4-methylphenol, 2-[3-(2H-benzotriazol-2-yl)-4-hydroxyphenyl]ethyl methacrylate, 2-(2H-benzotriazol-2-yl)-4-methyl-6-(2-propenyl)phenol, 2-(4-benzoyl-3-hydroxyphenoxy)ethyl acrylate, 3,9-bis(2,4-dicumylphenoxy)-2,4,8,10-tetraoxa-3,9-diphosphaspiro[5.5]undecane, bis(octadecyl)-hydroxylamine, 3,9-Bis(octadecyloxy)-2,4,8,10-tetraoxa-3,9-diphosphaspiro[5.5]undecane, bis(1-octyloxy-2,2,6,6-tetramethyl-4-piperidyl)sebacate, bis(2,2,6,6-tetramethyl-4-piperidyl)sebacate, 2-tert-butyl-6-(5-chloro-2H-benzotriazol-2-yl)-4-methylphenol, 2-tert-butyl-4-ethylphenol, 5-chloro-2-hydroxybenzophenone, 5-chloro-2-hydroxy-4-methylbenzophenone, 2,4-di-tert-butyl-6-(5-chloro-2H-benzotriazol-2-yl)phenol, 2,6-di-tert-butyl-4-(dimethylaminomethyl)phenol, 3',5'-dichloro-2'-hydroxyacetophenone, didodecyl 3,3'-thiodipropionate, 2,4-dihydroxybenzophenone, 2,2'-dihydroxy- 4,4'-dimethoxybenzophenone, 2,2'-dihydroxy-4-methoxybenzophenone, 2',4'-Dihydroxy-3'-propylacetophenone, 2,3-dimethylhydroquinone, 2-(4,6-diphenyl-1,3,5-triazin-2-yl)-5-[(hexyl)oxy]-phenol, ditridecyl 3,3'-thiodipropionate, 5-ethyl-1-aza-3,7-dioxabicyclo[3.3.0]octane, ethyl 2-cyano-3,3-diphenylacrylate, 2-ethylhexyl 2-cyano-3,3-diphenylacrylate, 2-ethylhexyl trans-4-methoxycinnamate, 2-ethylhexyl salicylate, methyl anthranilate, 2-methoxyhydroquinone, methyl-p-benzoquinone, 2,2'-methylenebis[6-(2H-benzotriazol-2-yl)-4-(1,1,3,3-tetramethylbutyl)phenol], 5,5'-methylenebis(2-hydroxy-4-methoxybenzophenone), methylhydroquinone, 4-nitrophenol sodium salt hydrate, octadecyl 3-(3,5-di-tert-butyl-4-hydroxyphenyl)propionate, pentaerythritol tetrakis(3,5-di-tert-butyl-4-hydroxyhydrocinnamate), 2-phenyl-5-benzimidazolesulfonic acid, poly[[6-[(1,1,3,3-tetramethylbutyl)amino]-s-triazine-2,4-diyl]-[(2,2,6,6-tetramethyl-4-piperidyl)imino]-hexamethylene-[(2,2,6,6-tetramethyl-4-piperidyl)imino], sodium d-isoascorbate monohydrate, tetrachloro-1,4-benzoquinone, triisodecyl phosphite, 1,3,5-trimethyl-2,4,6-tris(3,5-di-tert-butyl-4-hydroxybenzyl)benzene, tris(4-tert-butyl-3-hydroxy-2,6-dimethylbenzyl)isocyanurate, tris(2,4-di-tert-butylphenyl)phosphite, 1,3,5-tris(2-hydroxyethyl)isocyanurate, tris(nonylphenyl)phosphite, and the like.

Example 1

Comparative Example

A 500 ml glass flask (reactor) equipped with a magnetic stirring bar and a total condenser was charged with 100.0 g HCC-250fb (Honeywell, 99.9 wt %) and 0.026 g $FeCl_3$. The reactor was stirred and heated to 120°±2° C. via an oil bath. After 2 hours, the reactor was removed from the oil bath and cooled down to room temperature. Then the mixture in the reactor was filtered, washed with deionized (D.I.) water and dried with $MgSO_4$. By GC analysis, the reaction mixture contained 78.2 wt % of 1,1,3-trichloropropene, 2.1 wt % of HCC-250fb and 19.7 wt % of HBCs, representing a HCC-250fb conversion of 98.2 mol %, 1,1,3-trichloropropene selectivity of 87.8 mol %, and HBCs selectivity of 12.2 mol %.

Example 2

100.5 g HCC-250fb (Honeywell, 99.9 wt %), 0.025 g $FeCl_3$ and 0.011 g 2,6-di-tert-butyl-p-cresol (butylated hydroxytoluene or BHT) were charged into the reactor with the same reaction conditions and procedure followed as described in Example 1. By GC analysis, the reaction mixture contained 79.2 wt % of 1,1,3-trichloropropene, 2.1 wt % of HCC-250fb and 18.6 wt % of HBCs, representing a HCC-250fb conversion of 98.1 mol %, 1,1,3-trichloropropene selectivity of 88.5 mol % and HBCs selectivity of 11.5 mol %.

Example 3

The same apparatus as described in Example 1 was charged with 100.4 g HCC-250fb (Honeywell, 99.9 wt %), 0.026 g $FeCl_3$ and 0.026 g BHT. The same reaction conditions and procedure were followed as in Example 1. By GC analysis, the reaction mixture contained 72.7 wt % of 1,1,3-trichloropropene, 24.3 wt % of HCC-250fb and 2.8 wt % of HBCs, representing a HCC-250fb conversion of 79.3 mol %, 1,1,3-trichloropropene selectivity of 98.0 mol % and HBCs selectivity of 2.0 mol %.

Example 4

The same apparatus as described in Example 1 was charged with 100.1 g HCC-250fb (Honeywell, 99.9 wt %), 0.026 g $FeCl_3$ and 0.056 g BHT. The same reaction conditions and procedure were followed as in Example 1. By GC analysis, the reaction mixture contained 53.2 wt % of 1,1,3-trichloropropene, 46.1 wt % of HCC-250fb and 0.4 wt % of HBCs, representing a HCC-250fb conversion of 59.3 mol %, 1,1,3-trichloropropene selectivity of 99.5 mol % and HBCs selectivity of 0.4 mol %.

Example 5

The same apparatus as described in Example 1 was charged with 100.4 g HCC-250fb (Honeywell, 99.9 wt %), 0.026 g $FeCl_3$ and 0.108 g BHT. The same reaction conditions and procedure were followed as in Example 1. By GC analysis, the reaction mixture contained 20.4 wt % of 1,1,3-trichloropropene and 79.5 wt % of HCC-250fb with no HBCs detected, representing a HCC-250fb conversion of 24.3 mol %, 1,1,3-trichloropropene selectivity of 100.0 mol % and HBCs selectivity of 0.0 mol %.

Example 6

The same apparatus as described in Example 1 was charged with 100.3 g HCC-250fb (Honeywell, 99.9 wt %), 0.029 g $FeCl_3$ and 0.079 g 2,4-di-tert-butylphenol. The same reaction conditions and procedure were followed as in Example 1. By GC analysis, the reaction mixture contained 70.8 wt % of 1,1,3-trichloropropene, 26.3 wt % of HCC-250fb and 2.2 wt % of HBCs, representing a HCC-250fb conversion of 77.7 mol %, 1,1,3-trichloropropene selectivity of 98.3 mol % and HBCs selectivity of 1.7 mol %.

Example 7

The same apparatus as described in Example 1 was charged with 100.4 g HCC-250fb (Honeywell, 99.9 wt %), 0.026 g $FeCl_3$ and 0.01 g 2,6-di-tert-butylphenol. The same reaction conditions and procedure were followed as in Example 1. By GC analysis, the reaction mixture contained 75.3 wt % of 1,1,3-trichloropropene, 21.2 wt % of HCC-250fb and 3.3 wt % of HBCs, representing a HCC-250fb conversion of 81.9 mol %, 1,1,3-trichloropropene selectivity of 97.7 mol % and HBCs selectivity of 2.3 mol %.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. In the process of the catalytic dehydrochlorination of 1,1,1,3-tetrachloro-propane (HCC-250fb) to produce 1,1,3-trichloropropene and/or 3,3,3-trichloropropene, the improvement comprising the addition of one or more UV-stabilizer and/or anti-oxidant compounds, or mixtures thereof, into the dehydrochlorination reaction system to inhibit the formation of high boiling compounds, and wherein the product selectivity to 1,1,3-trichloropropene and/or 3,3,3-trichloropropene is at least about 50% or higher.

2. The process of claim 1, wherein the dehydrochlorination catalyst comprises one or more metal halides or mixtures thereof.

3. The process of claim 1, wherein the dehydrochlorination catalyst comprises $FeCl_3$.

4. The process of claim 3, wherein the dehydrochlorination reaction temperature is from 50° to 140° C.

5. The process of claim 3, wherein the dehydrochlorination reaction temperature is from 80° to 120° C.

6. The process of claim 3, wherein the dehydrochlorination reaction time is from 0.5 to 10 hours.

7. The process of claim 3, wherein the dehydrochlorination reaction time is from 1 to 4 hours.

8. The process of claim 3, wherein the weight ratio of the catalyst to the reactant 1,1,1,3-tetrachloropropane is from above 0 to about 5% by weight.

9. The process of claim 3, wherein the weight ratio of the catalyst to the reactant 1,1,1,3-tetrachloropropane is from 0.01% to 0.5% by weight.

10. In the process of the catalytic dehydrochlorination of 1,1,1,3-tetrachloro-propane (HCC-250fb) to produce 1,1,3-trichloropropene and/or 3,3,3-trichloropropene, the improvement comprising the addition of one or more UV-stabilizer and/or anti-oxidant compounds, or mixtures thereof, into the dehydrochlorination reaction system to inhibit the formation of high boiling compounds;
    wherein the dehydrochlorination catalyst comprises $FeCl_3$; and
    wherein the weight ratio of UV-stabilizer and/or anti-oxidant and/or their mixtures to the reactant 1,1,1,3-tetrachloropropane ranges from above 0 to about 2% by weight.

11. In the process of the catalytic dehydrochlorination of 1,1,1,3-tetrachloro-propane (HCC-250fb) to produce 1,1,3-trichloropropene and/or 3,3,3-trichloropropene, the improvement comprising the addition of one or more UV-stabilizer and/or anti-oxidant compounds, or mixtures thereof, into the dehydrochlorination reaction system to inhibit the formation of high boiling compounds;
    wherein the dehydrochlorination catalyst comprises $FeCl_3$; and
    wherein the weight ratio of UV-Stabilizer and/or anti-oxidant and/or their mixtures to the reactant 1,1,1,3-tetrachloropropane ranges from about 0.0001% to about 0.5%.

12. In the process of the catalytic dehydrochlorination of chlorinated alkanes to produce chlorinated alkenes, the improvement comprising the addition of one or more UV-stabilizer and/or anti-oxidant compounds, or mixtures thereof, into the dehydrochlorination reaction system to inhibit the formation of high boiling compounds, and
    wherein the UV-Stabilizer and/or anti-oxidant and/or their mixtures is selected from the group consisting of benzophenones, polyphenols, amines, hydroquinones, butylated hydroxy anisoles (BHA), thymols, and mixtures thereof; and wherein the weight ratio of UV-Stabilizer and/or anti-oxidant and/or their mixtures to the reactant 1,1,1,3-tetrachloropropane ranges from about 0 to about 2% by weight.

13. The process of claim 12, wherein the dehydrochlorination reaction system comprises the dehydrochlorination of 1,1,1,3-tetrachloropropane to produce 1,1,3-trichloropropene and/or 3,3,3-trichloropropene.

14. The process of claim 12, wherein the UV-Stabilizer and/or anti-oxidant and/or their mixtures is selected from the group consisting of methoxy-hydroquinones, triethylamines, di-isopropyl amines, and mixtures thereof.

15. A process for the catalytic dehydrochlorination of chlorinated alkanes to produce chlorinated alkenes using one or more metal halides or mixtures as the catalyst, comprising adding one or more UV-stabilizer and/or anti-oxidant compounds, or mixtures thereof, into the dehydrochlorination reaction system to improve the selectivity to the product chlorinated alkenes, wherein the UV-stabilizer and/or anti-oxidant compounds are selected from the group consisting of benzophenones, polyphenols, amines, hydroquinones, butylated hydroxy anisoles (BHA), thymols, and mixtures thereof; and wherein the weight ratio of UV-Stabilizer and/or anti-oxidant and/or their mixtures to the reactant 1,1,1,3-tetrachloropropane ranges from about 0 to about 2% by weight.

16. A process for the catalytic dehydrochlorination of chlorinated alkanes to produce chlorinated alkenes using one or more metal halides or mixtures as the catalyst, comprising adding one or more UV-stabilizer and/or anti-oxidant compounds, or mixtures thereof, into the dehydrochlorination reaction system to improve the selectivity to the product chlorinated alkenes, wherein the UV-stabilizer and/or anti-oxidant compounds are selected from the group consisting of benzophenones, polyphenols, amines, hydroquinones, butylated hydroxy anisoles (BHA), thymols, and mixtures thereof; and
    wherein the product selectivity is at least about 50% or higher.

17. The process of claim 16, wherein the product selectivity is at least about 70% or higher.

18. The process of claim 16, wherein the product selectivity is at least about 95% or higher.

19. The process of claim 15, wherein the UV-stabilizer and/or anti-oxidant compounds are selected from the group consisting of methoxy-hydroquinones, triethylamines, di-isopropyl amines, and mixtures thereof.

20. The process of claim 16, wherein the UV-stabilizer and/or anti-oxidant compounds are selected from the group consisting of methoxy-hydroquinones, triethylamines, di-isopropyl amines, and mixtures thereof.

* * * * *